(12) United States Patent
Fukasawa et al.

(10) Patent No.: US 10,537,242 B2
(45) Date of Patent: Jan. 21, 2020

(54) IMAGING APPARATUS

(71) Applicant: CANON KABUSHIKI KAISHA, Tokyo (JP)

(72) Inventors: Taro Fukasawa, Kawasaki (JP); Takashi Naba, Kawasaki (JP); Yasuhisa Inao, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 113 days.

(21) Appl. No.: 15/246,202

(22) Filed: Aug. 24, 2016

(65) Prior Publication Data

US 2017/0065169 A1 Mar. 9, 2017

(30) Foreign Application Priority Data

Sep. 4, 2015 (JP) .................. 2015-175020

(51) Int. Cl.
 *A61B 3/10* (2006.01)
 *A61B 3/14* (2006.01)
 *A61B 3/12* (2006.01)
 *A61B 3/00* (2006.01)

(52) U.S. Cl.
 CPC ............ *A61B 3/102* (2013.01); *A61B 3/0025* (2013.01); *A61B 3/1225* (2013.01); *A61B 3/14* (2013.01)

(58) Field of Classification Search
 CPC ............ G01B 9/02002; G01B 9/02069; G01B 9/02067; A61B 3/102; A61B 3/0025; A61B 3/1225; A61B 3/01; H03L 7/07; H03L 7/0805; H03L 7/093; H03L 7/104
 USPC ..................... 327/147, 156; 702/72; 351/206
 See application file for complete search history.

(56) References Cited

U.S. PATENT DOCUMENTS

2011/0178413 A1* 7/2011 Schmitt ............... A61B 5/0066
600/478

FOREIGN PATENT DOCUMENTS

| JP | 2002353812 A | 12/2002 |
|----|--------------|---------|
| JP | 2009156749 A | 7/2009 |
| JP | 2012-115578 A | 6/2012 |
| JP | 2012225926 A | 11/2012 |
| JP | 2014-016181 A | 1/2014 |
| JP | 2014200679 A | 10/2014 |

(Continued)

OTHER PUBLICATIONS

Hidekazu, et.al., "Optical coherence tomographic imaging apparatus", JP 2014-16181A, machine translation.*

*Primary Examiner* — Wen Huang
(74) *Attorney, Agent, or Firm* — Canon U.S.A., Inc. I.P. Division

(57) ABSTRACT

An imaging apparatus includes a converter configured to convert an analog signal obtained from detected interference light into a digital signal and a clock generator configured as an interferometer including an optical path through which part of light emitted from a light source passes, the optical path being split into a first optical path and a second optical path having an optical path length difference therebetween, to generate a clock used by the converter sampling the analog signal at a frequency corresponding to the optical path length difference. The converter includes n A/D converters, n being an integer of at least 2, and is configured to change phases of n clocks obtained from the clock to produce a phase difference therebetween, and to generate a clock having an n-times frequency from the n clocks and n analog signals obtained from the analog signal using the n A/D converters.

32 Claims, 9 Drawing Sheets

(56) References Cited

FOREIGN PATENT DOCUMENTS

| | | |
|---|---|---|
| JP | 2015-117978 A | 6/2015 |
| JP | 2015102537 A | 6/2015 |
| JP | 5987186 B1 | 9/2016 |
| WO | 2014038056 A1 | 3/2014 |

* cited by examiner

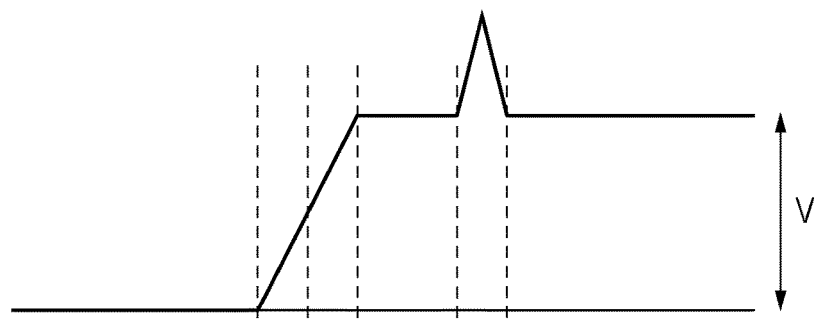
FIG. 9A
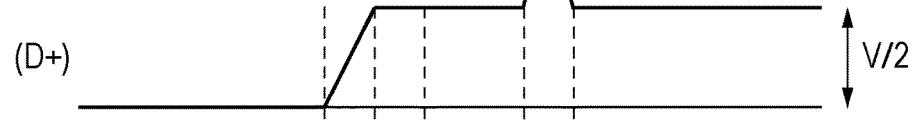
FIG. 9B (D+)
FIG. 9C (D-)
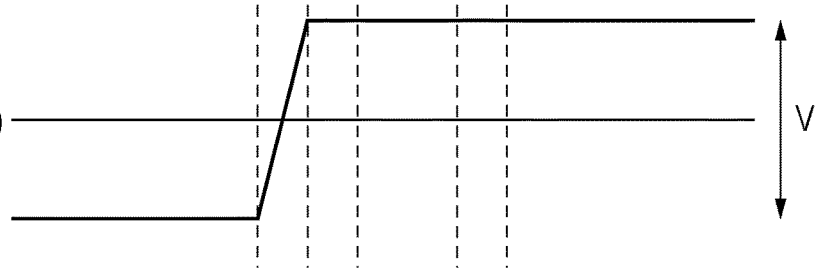
FIG. 9D (D+)-(D-)

IMAGING APPARATUS

BACKGROUND OF THE INVENTION

Field of the Invention

The present invention relates to an imaging apparatus that captures optical coherence tomographic images.

Description of the Related Art

Imaging apparatuses that employ optical coherence tomography (hereinafter referred to as OCT) are being developed (hereinafter, an imaging apparatus that employs OCT is referred to as an OCT apparatus). An OCT apparatus irradiates an object with light while changing the wavelength of the irradiation light, makes reflection light beams returned from different depths of the object interfere with reference light, and analyzes frequency components contained in the intensity of the resulting interference light (that is, the interference spectrum) to thereby obtain a tomographic image of the object. OCT apparatuses are used in fundus examinations, for example.

In fundus examinations, it is basically desirable to find any lesion located away from the macula in order to detect ocular diseases earlier and to start a treatment. To meet such a desire, OCT apparatuses used in fundus examinations are also expected to have a wider angle of view currently.

To attain the wider angle described above, Japanese Patent Laid-Open No. 2012-115578 discloses a typical configuration of a swept-source OCT (SS-OCT) apparatus as described above having a typical sample rate and a technique for creating a tomographic image of a wide area by combining together a plurality of tomographic images to widen the area of the fundus which is observable on the tomographic image. Although an expensive swept light source that can generate light having a long coherence length and an expensive analog/digital (A/D) converter having a wide analog band need not be used according to Japanese Patent Laid-Open No. 2012-115578, image processing for combining together the plurality of tomographic images takes longer and is troublesome, which is a shortcoming.

Although Japanese Patent Laid-Open No. 2014-016181 does not address the above-described issue concerning the wider angle of view, it illustrates a configuration in which two A/D converters are used while switching between the two A/D converters is performed to implement an interleaving operation, for example, in order to configure an OCT apparatus. However, Japanese Patent Laid-Open No. 2014-016181 only illustrates the configuration for implementing an interleaving operation and does not indicate that this configuration is used to address an issue concerning comprehensively obtaining, with a single operation, a tomographic image in a depth range associated with a wider angle. Moreover, Japanese Patent Laid-Open No. 2014-016181 does not disclose a method for correctly maintaining an equal wavenumber property of the sampling timing required for SS-OCT in the process of transmitting the clock.

SUMMARY OF THE INVENTION

An imaging apparatus according to one aspect of the present invention is an image apparatus including a light source, an interference unit, a scanning unit, a detector, a converter, a clock generator, and a tomographic image obtaining unit. The light source is configured to emit light while sweeping a wavelength of the light. The interference unit is configured to split the light emitted from the light source into irradiation light with which a fundus is irradiated and reference light and to generate interference light obtained by interference of reflection light reflected from the fundus irradiated with the irradiation light with the reference light. The scanning unit is configured to scan the irradiation light on the fundus. The detector is configured to detect the interference light. The converter is configured to convert an analog signal generated from the interference light into a digital signal. The clock generator is configured as an interferometer including an optical path through which part of the light emitted from the light source passes, the optical path being split into a first optical path and a second optical path having an optical path length difference relative to the first optical path, to generate a clock used by the converter sampling the analog signal at a frequency corresponding to the optical path length difference. The tomographic image obtaining unit is configured to obtain a tomographic image of the fundus by using the digital signal converted from the analog signal sampled by the converter in accordance with the generated clock. The scanning unit is configured to scan the irradiation light across the fundus over a scan angle equal to or larger than 47 degrees in air. The converter includes n analog/digital converters, n being an integer equal to or larger than 2, and is configured to change phases of n clocks obtained from the clock having the frequency corresponding to the optical path length difference to produce a phase difference between the phases, and to generate a clock having a frequency n times the frequency corresponding to the optical path length difference from the n clocks and n analog signals obtained from the analog signal by using the n analog/digital converters.

Further features of the present invention will become apparent from the following description of exemplary embodiments with reference to the attached drawings.

BRIEF DESCRIPTION OF THE DRAWINGS

FIGS. 9A to 9D are diagrams for describing a clock corresponding to the frequency of the k-clock being generated as a differential signal according to the present embodiment.

DESCRIPTION OF THE EMBODIMENTS

Figure 1:
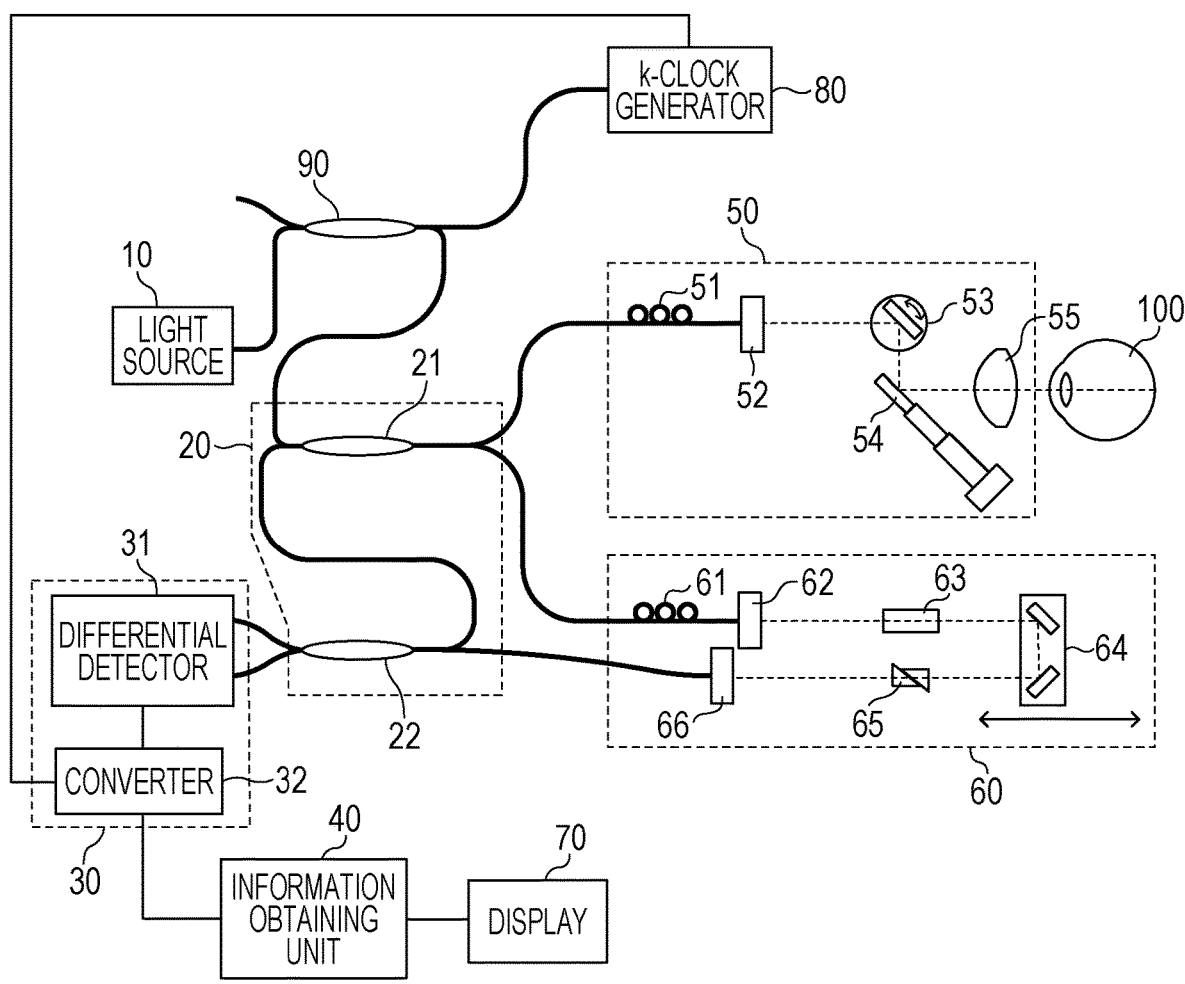
FIG. 1 is a schematic diagram illustrating an example of an OCT apparatus according to the present embodiment.

Typically, the eyeball is substantially spherical, and therefore, the optical path length of irradiation light in a central portion of the fundus is significantly different from that in a peripheral portion thereof. Accordingly, the desire for a wider angle also creates a desire for comprehensively obtaining a tomographic image of the fundus in a desired depth range with a single operation. With the configuration of an OCT apparatus according to the related art, it is difficult to comprehensively obtain a tomographic image of the fundus in a desired depth range with a single operation when a wide area of the fundus is scanned.

The above-described desire is, in a case of an OCT apparatus using a swept light source (that is, a swept-source OCT apparatus or an SS-OCT apparatus), equivalent to sampling an interference signal that is detected by an optical detector as an analog signal and that changes over time, the sampling being performed by an A/D converter at a high rate. To generate a sample clock in a typical SS-OCT apparatus, it is common practice to separately configure an interferometer for clock generation having a larger optical path length difference and to use the output from the interferometer in addition to an interferometer that generates interference light to be sampled. To increase the sample rate in the SS-OCT apparatus configured as described above, it is necessary to further increase the optical path length difference of the interferometer for clock generation.

In this case, an expensive swept light source capable of generating light having a long coherence length that causes interference even if the optical path length difference is large is used. Further, an expensive A/D converter having a wide analog band is used to perform such high-speed sampling.

To address the issues described above, the present embodiment provides a sampling method for comprehensively obtaining a tomographic image of the fundus in a desired depth range with a single scan operation over a wide area of the fundus.

An imaging apparatus according to the present embodiment includes a converter that converts an analog signal obtained by a detector detecting interference light into a digital signal. The imaging apparatus according to the present embodiment includes a clock generator that generates a clock used to sample the analog signal at a frequency corresponding to an optical path length difference. The clock generator is configured as an interferometer including an optical path through which part of light emitted from a light source passes, the optical path being split into a first optical path and a second optical path having an optical path length difference relative to the first optical path. The converter includes n (n is an integer equal to or larger than 2) A/D converters. The converter changes the phases of n clocks obtained from the clock having the frequency corresponding to the optical path length difference to produce a phase difference between the phases. The converter is configured to generate a clock having a frequency n times the frequency corresponding to the optical path length difference from the n clocks and n analog signals obtained from the analog signal by using the n A/D converters. Accordingly, it is possible to provide a high-speed and low-cost sampling method for comprehensively obtaining a tomographic image of the fundus in a desired depth range with a single scan operation over a wide area of the fundus.

Hereinafter, an embodiment of the present invention will be described with reference to the drawings. An embodiment described below is not intended to limit the present invention described in the appended claims, and all of the combinations of features described in the present embodiment are not necessarily essential to a solution provided by the present invention. For example, an OCT apparatus according to the present embodiment is configured by using a Mach-Zehnder interferometer; however, the present invention is not limited to this. The OCT apparatus may be configured by using a Michelson interferometer. The OCT apparatus according to the present embodiment is configured to change the reference optical path length; however, the present invention is not limited to this. The OCT apparatus is configured to change the optical path length difference between the reference light and the measurement light. For example, the reference optical path length may be fixed while the measurement optical path length may be changed. A light source 10 in the present embodiment is not limited to a specific light source as long as the light source changes the wavelength of the light. An external-resonator-type swept light source that uses a diffraction grating, a prism, and so on, or an external-resonator-type light source of any type using a cavity-length-variable Fabry-Perot tunable filter may be used, for example. Alternatively, a superstructure-grating distributed Bragg reflector (SSG-DBR) that changes the wavelength by using a sampled grating, a tunable vertical-cavity surface-emitting laser (VCSEL) using the micro-electro-mechanical systems (MEMS) mechanism (MEMS-VCSEL), or the like may be used. Also, a fiber laser may be used. The fiber laser may be based on a dispersion tuning scheme or a Fourier domain mode locking scheme. Examples of the external-resonator-type swept light source using a diffraction grating, a prism, and so on include a swept light source in which a resonator is equipped with a diffraction grating, the light is separated by the diffraction grating, and the wavelength of the emitted light is continuously changed by using a polygon mirror or a stripe-shaped reflection mirror provided on a rotating disk. Configuration of SS-OCT FIG. 1 is a diagram illustrating an example configuration of an imaging apparatus based on OCT (OCT apparatus) according to the present embodiment. The OCT apparatus includes the light source 10 that sweeps the optical frequency of the emitted light, an OCT interference unit 20 that generates interference light, a detector 30 that detects the interference light, and an information obtaining unit 40 that obtains information about the fundus of an object 100. The information obtaining unit 40 also functions as a tomographic image obtaining unit (image generation unit) that obtains (generates) a tomographic image of the fundus. The OCT apparatus further includes a measurement arm 50 and a reference arm 60.

The OCT interference unit 20 includes couplers 21 and 22. The coupler 21 splits light emitted from the light source 10 into irradiation light with which the fundus is irradiated and reference light. The irradiation light passes through the measurement arm 50, and the object 100 is irradiated therewith. More specifically, the irradiation light that enters the measurement arm 50 passes through a polarization controller 51 at which the polarization state thereof is adjusted, and is thereafter emitted from a collimator 52 as spatial light. Thereafter, the irradiation light passes through an X-axis scanner 53, a Y-axis scanner 54, and a focus lens 55, and the fundus of the object 100 is irradiated therewith. The X-axis scanner 53 and the Y-axis scanner 54 constitute a scanning unit having a function of scanning the fundus with the irradiation light. With the scanning unit, a position on the fundus which is irradiated with the irradiation light can be changed. The back-scattered light (reflection light) from the fundus passes through the focus lens 55, the Y-axis scanner 54, the X-axis scanner 53, the collimator 52, and the polarization controller 51, is emitted from the measurement arm 50, and enters the coupler 22 via the coupler 21.

On the other hand, the reference light passes through the reference arm 60 and enters the coupler 22. More specifically, the reference light that enters the reference arm 60 passes through a polarization controller 61 at which the polarization state thereof is adjusted, and is thereafter emitted from a collimator 62 as spatial light. Thereafter, the reference light passes through a dispersion compensation glass component 63, an optical-path-length adjusting optical system 64, and a dispersion adjusting prism pair 65, enters an optical fiber via a collimator lens 66, is emitted from the reference arm 60, and enters the coupler 22.

The reflection light from the object 100 which passes through the measurement arm 50 and the reference light which passes through the reference arm 60 interfere with each other at the coupler 22. Then, the resulting interference light is detected by the detector 30. The detector 30 includes a differential detector 31 and a converter 32 that includes n (n is an integer equal to or larger than 2) A/D converters. In the detector 30, the differential detector 31 detects interference light beams separated immediately after the interference light has been generated at the coupler 22. Then, the differential detector 31 converts the OCT interference signal into an electrical signal (analog signal), and the converter 32 converts the electrical signal into a digital signal. The digital signal is sent to the information obtaining unit 40 at which a frequency analysis, such as Fourier transform, is performed on the digital signal to thereby obtain information about the fundus. The obtained information about the fundus is displayed on a display 70 as a tomographic image.

The imaging apparatus according to the present embodiment may further include an analysis unit that analyzes the obtained tomographic image to perform segmentation into a plurality of layers, and the information obtaining unit 40 may function as the analysis unit, for example. In this case, the imaging apparatus may further include an image generation unit that generates a planar image along any of the plurality of layers in accordance with an analysis result from the analysis unit, and the information obtaining unit 40 may function as the image generation unit, for example. The imaging apparatus may further include a display controller that displays the planar image and the tomographic image on the display 70 while the positions of the macula and the optic disc of the fundus which are included in the planar image are associated with the positions of the macula and the optic disc of the fundus which are included in the tomographic image, and the information obtaining unit 40 may function as the display controller, for example. Accordingly, it is possible to observe the planar image along any of the plurality of layers over a wide angle of view, resulting in increased diagnostic efficiency and diagnostic accuracy. The imaging apparatus may further include a computation unit that generates curvature information about the fundus including the macula and the optic disc of the fundus by using a tomographic image of the macula and the optic disc of the fundus, and the information obtaining unit 40 may function as the computation unit, for example. Accordingly, it is possible to quantitatively evaluate the curvature of the fundus over a wide angle of view, resulting in increased diagnostic efficiency and diagnostic accuracy. To obtain a tomographic image of the fundus including the macula and the optic disc, the scanning unit may be controlled so that the macula and the optic disc are irradiated with the irradiation light with a single scan operation. Alternatively, a 3D tomographic image of the fundus may be obtained, and thereafter, a tomographic image including the macula and the optic disc may be recreated from the 3D tomographic image.

Figure 5A:
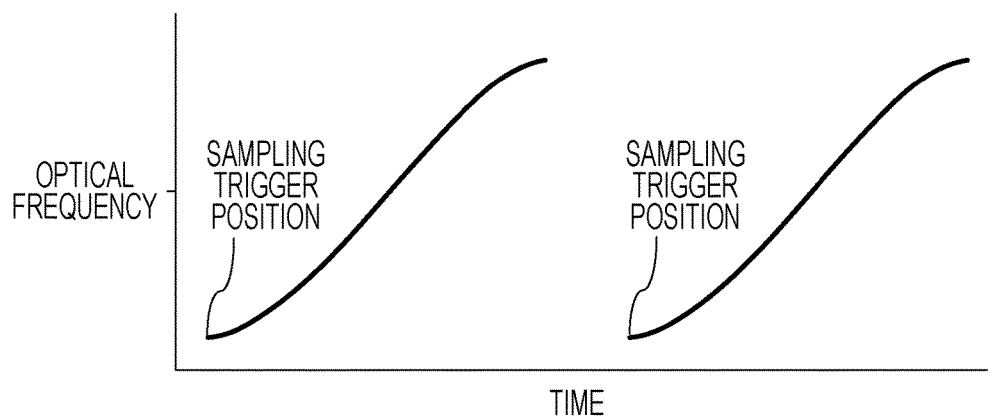
FIG. 5A is a diagram for describing changes in the optical frequency of a swept light source.

Sampling of interference light is performed on the basis of a clock at equal optical frequency (equal wavenumber) intervals, namely, a k-clock signal, issued from a k-clock generator 80 provided outside the light source 10. In OCT based on a Fourier domain scheme, such as SS-OCT, it is essential to perform sampling at equal wavenumber intervals in order to obtain image quality sufficient for diagnoses. Therefore, in SS-OCT, it is common practice to provide the k-clock generator 80 as in the present embodiment. If the optical frequency of light emitted from the light source 10 linearly changes relative to time with accuracy without using the k-clock, for example, sampling at equal time intervals causes no problem in principle. However, as schematically illustrated in FIG. 5A, a typical swept light source performs wavelength sweeping by a driving mechanism changing the cavity length. Therefore, the optical frequency is nonlinear relative to time, and stable sweeping is extremely difficult. Further, the optical frequency may shift due to a mode hop (an event in which the wavelength changes non-continuously at a certain timing) that occurs on some occasions, and therefore, it is difficult to obtain accurate distance information with sampling at equal time intervals. However, the present invention is not limited to the above-described sampling, and may be configured so that sampling at equal intervals is performed, interpolation or the like is performed, and conversion from the wavenumber space into the real space is thereafter performed, for example. To split the light emitted from the light source 10 and to direct part of the light into the k-clock generator 80, a coupler 90 is provided. The k-clock generator 80 and the coupler 90 may be built into the light source 10.

The process described above is a process for obtaining information about a cross section at a certain point of the object 100, and such a process for obtaining information about a cross section in the depth direction of the object 100 is called an A-scan. A scan for obtaining information about a cross section of the object in a direction orthogonal to the direction of the A-scan, that is, a scan for obtaining a 2D image, is called a B-scan. A scan performed in a direction orthogonal to both the direction of the A-scan and the direction of the B-scan is called a C-scan. In a case of performing a 2D raster scan on the fundus plane for obtaining a 3D tomographic image, a high-speed scanning direction corresponds to the B-scan, and a low-speed scanning direction that is orthogonal to the direction of the B-scan corresponds to the C-scan. A 2D tomographic image is obtained by performing an A-scan and a B-scan, and a 3D tomographic image is obtained by performing an A-scan, a B-scan, and a C-scan. A B-scan and a C-scan are performed by using the X-axis scanner 53 and the Y-axis scanner 54 described above.

Note that the X-axis scanner 53 and the Y-axis scanner 54 are constituted by polarization mirrors that are arranged so that their rotation axes are orthogonal to each other. The X-axis scanner 53 is responsible for a scan in an X-axis direction, and the Y-axis scanner 54 is responsible for a scan in a Y-axis direction. The X-axis direction and the Y-axis direction are directions perpendicular to the eye axis direction of the eyeball and are orthogonal to each other. The line scanning directions of a B-scan and a C-scan need not match the X-axis direction and the Y-axis direction. Therefore, the line scanning directions of a B-scan and a C-scan can be determined as appropriate in accordance with a 2D tomographic image or a 3D tomographic image that is to be captured.

Figure 2A:
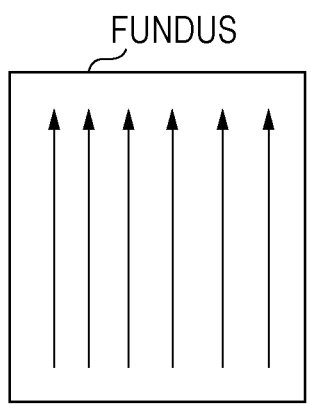
FIGS. 2A to 2D are schematic diagrams illustrating example methods of scanning irradiation light performed by a scanning unit of the OCT apparatus according to the present embodiment.
Figure 2B:
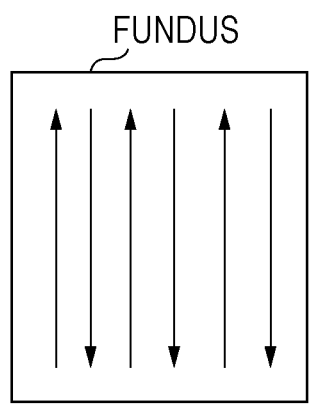
Figure 2C:
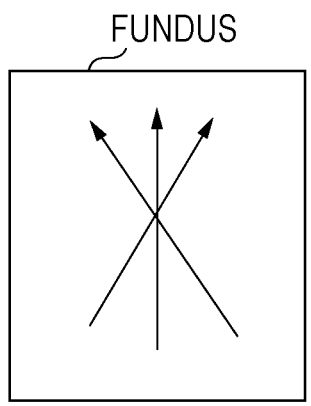
Figure 2D:
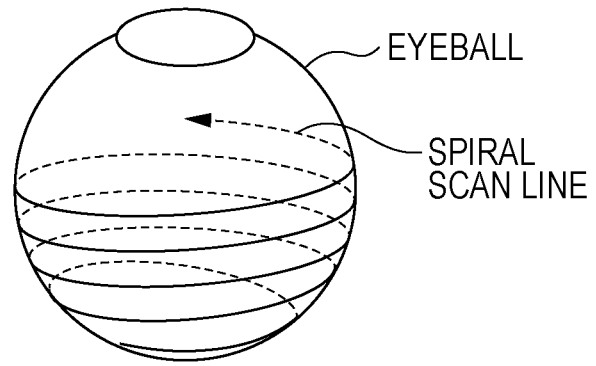

By driving both the X-axis scanner 53 and the Y-axis scanner 54 and changing the angles of the polarization mirrors, various scans can be performed. For example, raster scans as illustrated in FIGS. 2A and 2B may be performed, or a scan as illustrated in FIG. 2C may be performed in which the scan line passes through one point (the macula, for example) of the eyeball a plurality of times. A spiral scan centered around one point (the macula, for example) of the eyeball as illustrated in FIG. 2D may be performed.

Scan Angle

Figure 3:
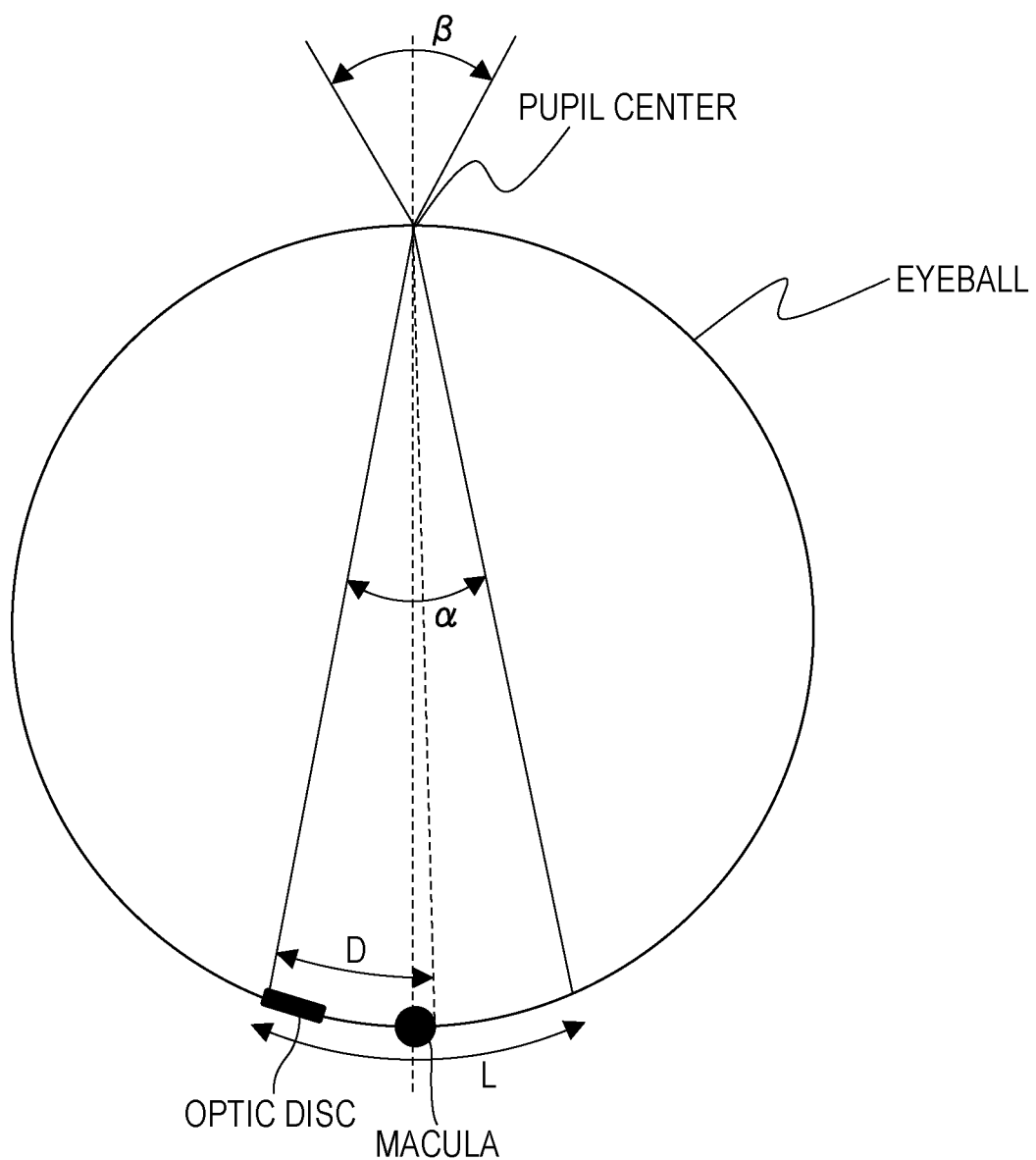
FIG. 3 is a schematic diagram of an eyeball relating to the present embodiment.

Regarding fundus examinations, it is desirable to capture an image over a wide angle as described above. A range (scan angle) over which the irradiation light of the OCT apparatus is scanned and which is used to meet the desire is described with reference to a simple human eye model illustrated in FIG. 3. FIG. 3 is a schematic diagram of an eyeball while the eyeball is assumed to be spherical. The macula is located on the fundus on the visual axis that extends substantially along a line passing through the pupil center of the eyeball, and the optic disc is located a short distance away from the macula. The macula and the optic disc are especially important regions in the fundus. Capturing an image over a wide angle means capturing an image of the macula, the optic disc, and their peripheral portion with a single scan operation.

Regarding the fundus of a normal adult, the distance D between the macula and the optic disc is about 5.75 mm. The irradiation light is emitted to enter the pupil center of the eyeball and to circle around and scan the fundus. In a case of capturing an image of an area centered around the macula and including the optic disc with a single scan operation, the length L of the shortest curve that connects the macula and the optic disc, namely, the image capture range, is about 14 mm but takes into consideration variations among individuals. Here, the deflection angle of measurement light that is emitted to enter the pupil center and circle around the fundus is denoted by α, the deflection angle corresponding to the image capture range. The diameter of the eyeball of an adult is about 24 mm on average. Therefore, to set the image capture range L to 14 mm or more, the deflection angle α is 33.4 degrees or more. When this angle is represented as the deflection angle β of the irradiation light in air which is incident on the pupil center while the average refractive index within the eyeball is assumed to be 1.38, the deflection angle β is about 47 degrees (arcsin(1.38×sin(33.4 degrees/2))×2≅47 degrees). That is, to capture an image of the macula and the optic disc simultaneously while the image is centered around the macula, in a case of lineally scanning the fundus with irradiation light, the angle range for scanning the fundus is 47 degrees or more in terms of the angle in air. Hereinafter, the angle range for scanning the fundus in the case of linearly scanning the fundus with irradiation light in terms of the angle in air is assumed to be the angle of view. That is, the deflection angle β is specified as the angle of view.

Figure 4:
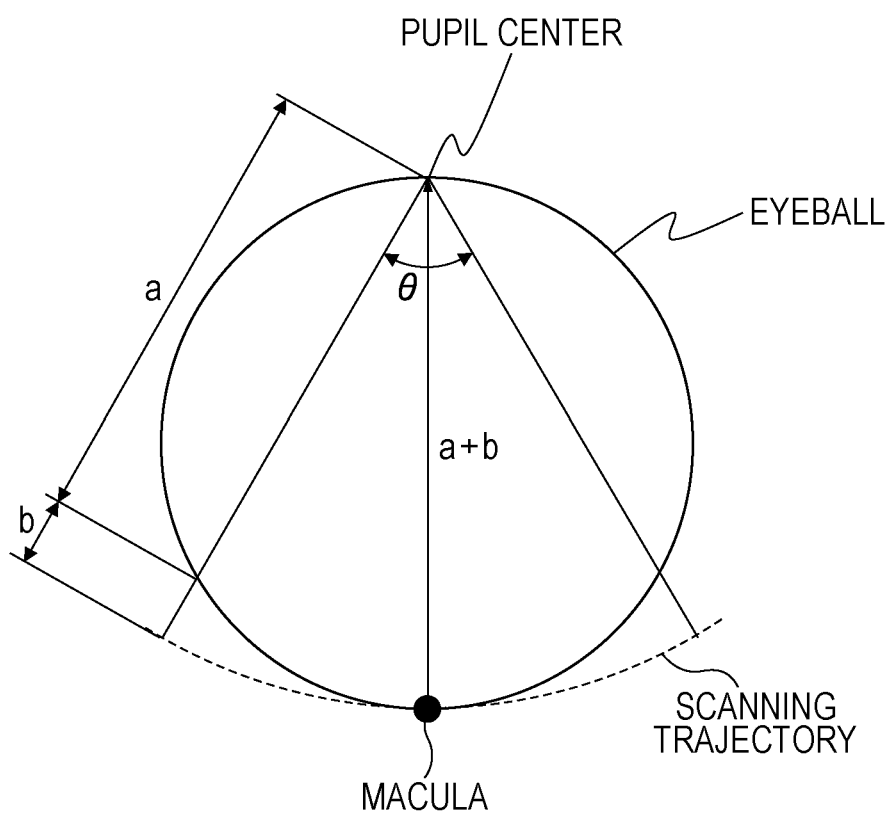
FIG. 4 is a diagram for describing the issue concerning a wider angle of view relating to the present embodiment.

Now, an issue that may arise when a scan is performed over the above-described deflection angle β is described with reference to FIG. 4. FIG. 4 is a schematic diagram of an eyeball while the eyeball is assumed to be spherical as in FIG. 3. The dashed line in FIG. 4 represents a scanning trajectory. As illustrated in FIG. 4, the physical distance from the pupil center to the outer layer of the eyeball, namely, the fundus, is equal to a+b at the macula and is equal to a at a position located away from the macula (that is, a position corresponding to the angle θ/2). The distances a and b are expressed by the following expressions by using the length T that is the eye axis length and the deflection angle θ within the eyeball:

$$a = T \times \cos(\theta/2) \qquad \text{expression 1,}$$

$$a + b = T \qquad \text{expression 2.}$$

As described above, the distance from the pupil center to the macula is different from the distance from the pupil center to the position away from the macula by b. The value of b increases as the angle θ becomes larger. Accordingly, an OCT apparatus for fundus examinations having a wide angle of view, the optical path length from the pupil center to the macula is significantly different from the optical path length from the pupil center to a peripheral position that is away from the macula. The eye axis lengths T of adults significantly vary among individuals, and the range of the eye axis length T into which the eye axis lengths of 95% of adults fall is between and inclusive of 21 mm and 28 mm. Here, if the maximum value of the range, namely, 28 mm, is used as the value of the eye axis length T, and the deflection angle θ within the eyeball is assumed to be 33.4 degrees, the value of b is about 1.2 mm from expressions 1 and 2.

Fundus tissues observed by using an OCT apparatus for fundus examinations are the retina in the vicinity of the surface of the fundus and the choroid lying behind the retina. The retina has a maximum thickness of about 0.50 mm, and the choroid has a maximum thickness of about 0.30 mm. Therefore, an OCT apparatus for fundus examinations should be capable of capturing images of a portion at the depth of at least 0.80 mm. That is, the surface of the fundus and the choroid have a distance difference of 0.8 mm therebetween.

Therefore, to capture an image of the macula and the optic disc with a single scan operation and to obtain information about the vicinity of the surface of the optic disc and about the choroid lying behind the macula, a distance difference of about 4.0 mm (2×(b+0.80)≅4.0) is used. This distance difference corresponds to about 5.5 mm (4.0 mm×1.38≅5.5 mm) in terms of the optical path length difference in air. That is, if the angle of view is assumed to be 47 degrees or more, the depth range of tomographic information (namely, the optical path length difference) that is attained is 5.5 mm in air. In a case where only a depth range of less than 5.5 mm is attained, a problem may arise in which the image is folded in the peripheral portion of the fundus, and image capturing might not be correctly performed. In general, regarding existing OCT apparatuses available on the market, the scan angle for scanning the fundus is set to about 40 degrees in terms of the angle in air, and the depth range (the distance in the depth direction of the tomographic image) is set to about 2.6 mm in terms of the range within the eyeball, or about 3.6 mm in terms of the range in air, to capture an image that includes from the choroid to the boundary of the sclera. Therefore, it is difficult to widen the angle of view to 47 degrees or more.

K-Clock Generator

Figure 5B:
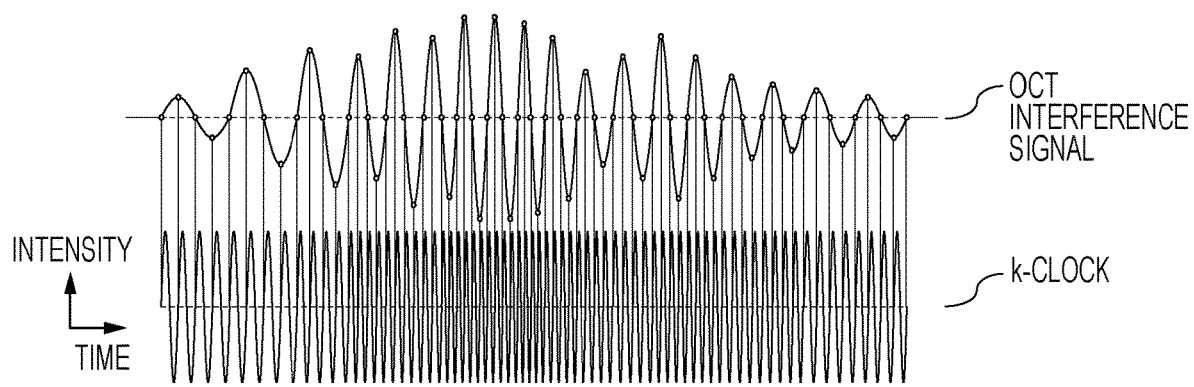
FIG. 5B is a diagram for describing a k-clock according to the present embodiment.
Figure 6:
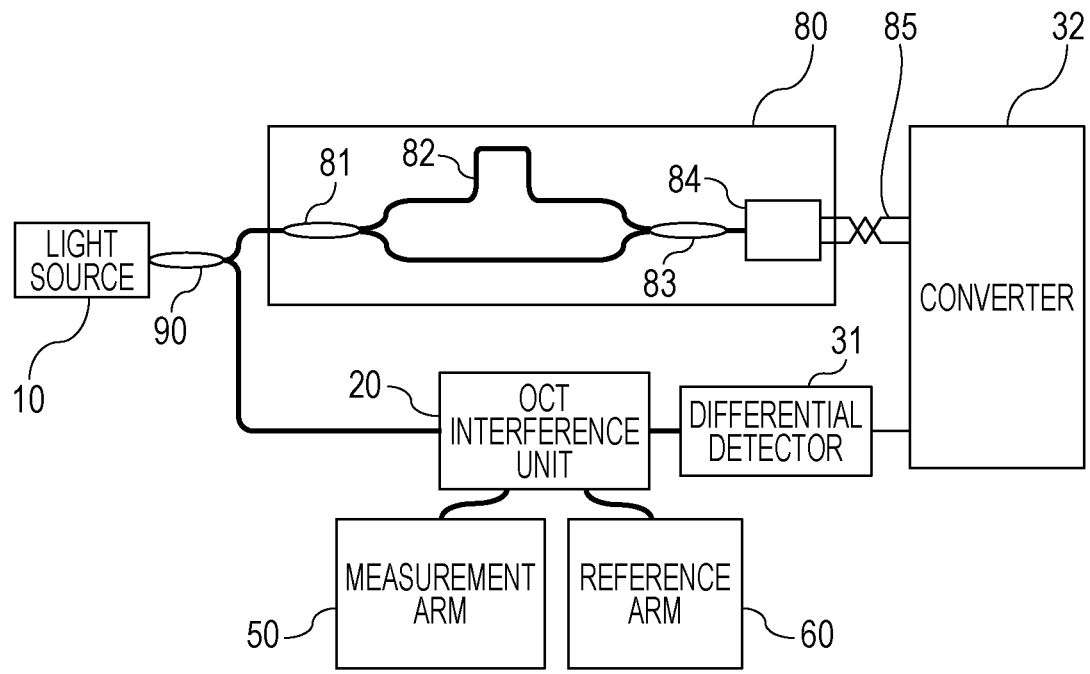
FIG. 6 is a schematic diagram of a k-clock generator according to the present embodiment.

Now, the k-clock for attaining the desired depth range is described with reference to FIG. 6. The reference numerals in FIG. 6 correspond to those in FIG. 1. Light emitted from the light source 10 is split at the coupler 90 having a split ratio of 95 to 5, for example, and part of the light enters the k-clock generator 80 as split light. The split light is further split at a coupler 81 and is directed to two optical paths, which are formed as a first optical path and a second optical path. The first optical path and the second optical path are provided to have an optical path length difference 82 therebetween, and the light beams passing through the two optical paths are made to interfere with each other at a coupler 83. Accordingly, a k-clock interferometer is configured. A k-clock interference signal generated at the k-clock interferometer takes the form of a sine wave as the optical frequency changes over time. As the optical frequency changes, the cycle of the sine wave also changes over time. The zero-crossing point or the peak point of the sine wave illustrated in FIG. 5B appears at equal wavenumber intervals. Therefore, if sampling is performed by using the zero-crossing point or the peak point as the clock position, an OCT interference signal in the wavenumber space can be obtained.

The amplitude of the k-clock interference signal is corrected by using an amplifier or the like to an amplitude and a voltage appropriate to the sample clock used by the converter 32 to sample the OCT interference signal.

Figure 7A:
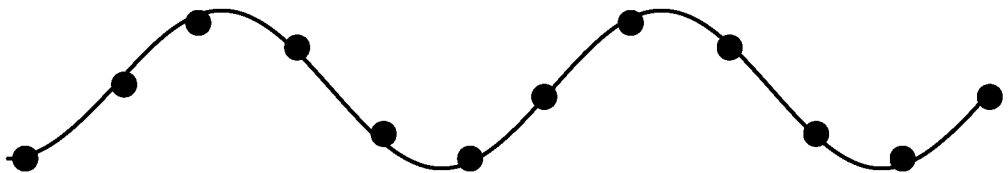
FIGS. 7A and 7B are diagrams for describing a sampling theorem relating to the present embodiment.
Figure 7B:
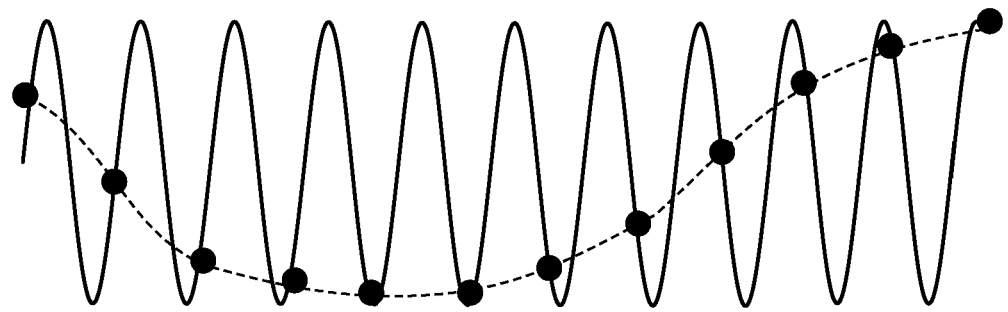

The frequency of the k-clock is a sampling frequency for the OCT interference signal, and therefore, the frequency of the k-clock is selected on the basis of a sampling theorem. For example, in a case where the frequency of the OCT interference signal is equal to or smaller than half the frequency of the k-clock as illustrated in FIG. 7A, the original signal can be reproduced. In a case where the frequency of the OCT interference signal is equal to or larger than half the frequency of the k-clock as illustrated in FIG. 7B, a false signal is obtained. Therefore, the frequency of the k-clock is provided equal to or larger than twice the frequency of the OCT interference signal.

To provide a desired frequency to the k-clock generated from the output of the k-clock interferometer using the same light source as that for the OCT interference signal, an appropriate optical path length difference is provided to the k-clock interferometer. The sample optical path of an OCT interferometer is usually configured as a double path that is constituted by an optical path through which irradiation light with which the fundus is irradiated passes and an optical path through which reflection light returns from the fundus. In contrast, the optical path of the k-clock interferometer of the present embodiment is configured as a single path in which light is split, the split light beams pass through optical paths having an optical path length difference therebetween, and thereafter the split light beams are combined without being reflected, as illustrated in FIG. 6. Therefore, in a case where it is desirable to set the depth range of the tomographic image to 5.5 mm or more in air (4.0 mm or more within the eyeball), the optical path length difference 82 for the k-clock is increased to a value four times the value of 5.5 mm or more, namely, 22 mm or more in air. That is, the optical path length difference 82 for the k-clock is set to a value equal to or larger than four times the depth range.

Figure 8A:
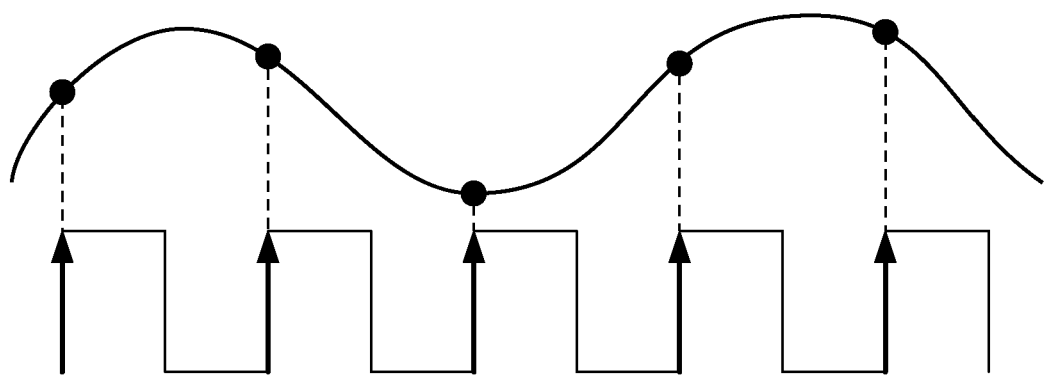
FIGS. 8A and 8B are diagrams for describing interleaving according to the present embodiment.
Figure 8B:
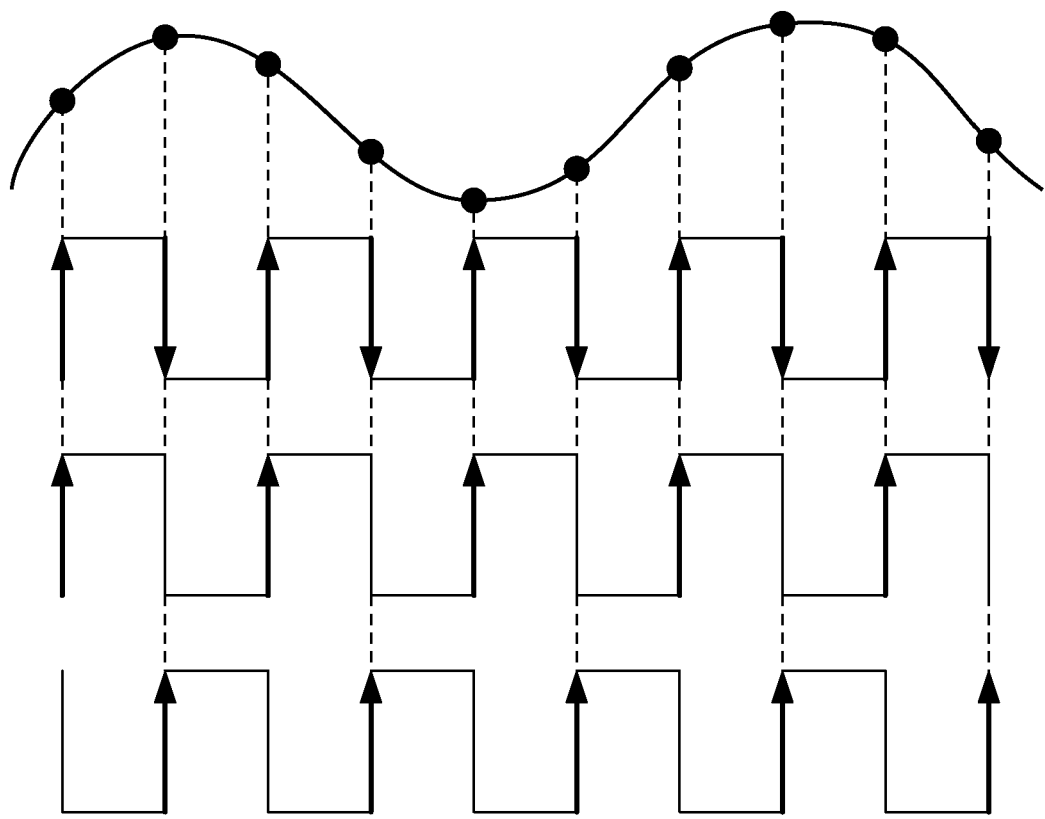
Figure 10:
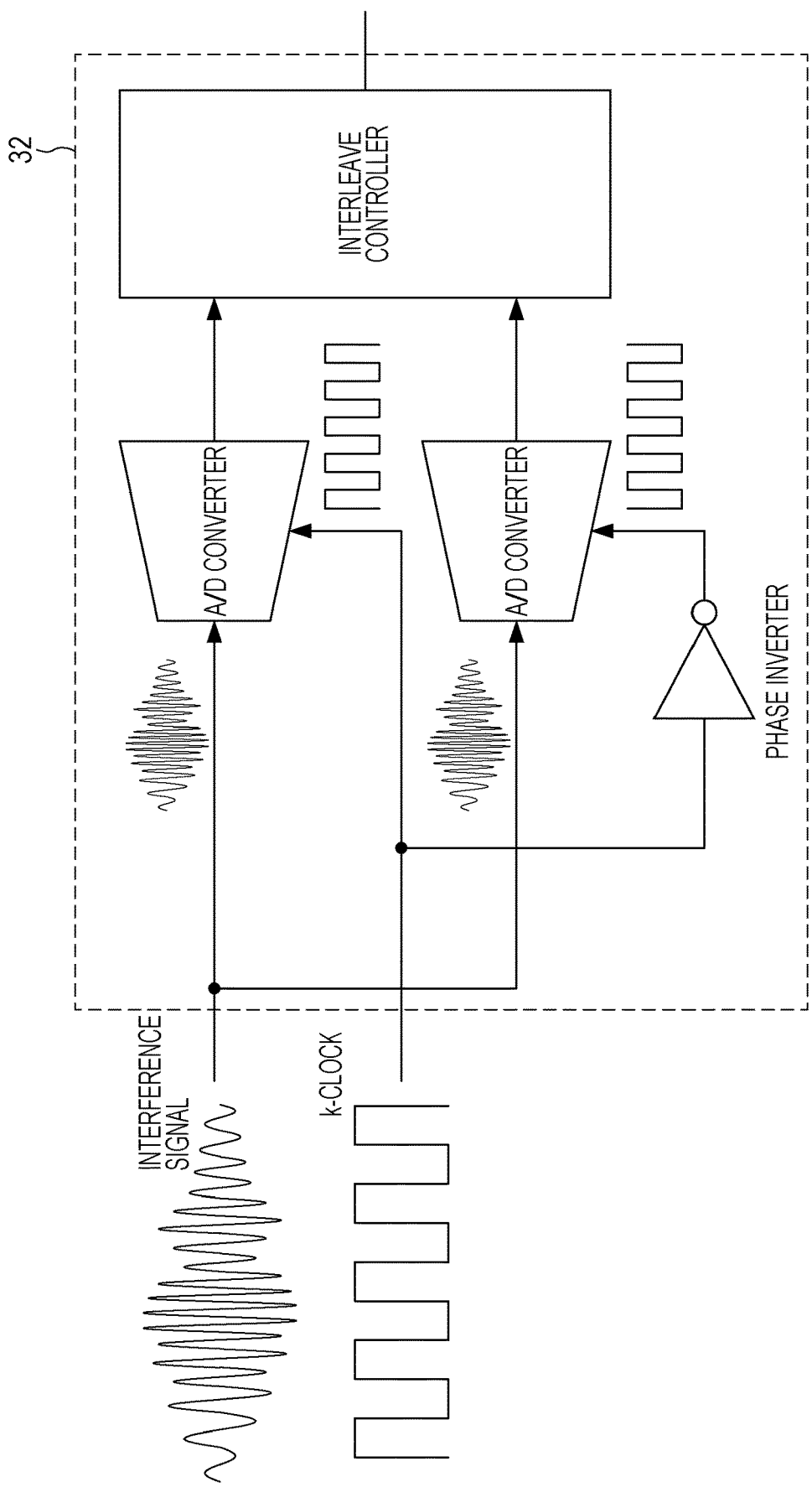
FIG. 10 is a schematic diagram illustrating a circuit configuration for interleaving and the states of an interference signal and the k-clock according to the present invention.

Optical Path Length Difference of Interferometer in K-clock Generator and Interleaving However, a swept light source that can generate light having a long coherence length as described above is difficult to manufacture and is extremely expensive, and therefore, such a swept light source is not preferable to general ophthalmological devices. Accordingly, in the SS-OCT apparatus according to the present embodiment, sampling is performed by performing an interleaving operation. Interleaving is a technique in which a single signal is sampled by using the converter 32 that includes n (n is an integer equal to or larger than 2) A/D converters. In general A/D conversion, a signal is obtained at the rising edge, as illustrated in FIGS. 8A and 8B, or at the falling edge of the clock, as illustrated in FIG. 8B. In interleaving, two clocks having phases shifted from each other by 180 degrees using a phase inverter circuit or the like are provided to two A/D converters, and signals are obtained at both the rising edge and the falling edge, as illustrated in FIG. 8B, to thereby attain a double sampling speed. That is, as illustrated in FIG. 10, the converter 32 is configured to divide a clock that corresponds to the frequency of the k-clock interferometer into n clocks that correspond to the n A/D converters, and to generate a clock having a frequency n times the frequency of the k-clock interferometer by using the divided n clocks. Note that FIG. 10 is a schematic diagram illustrating a circuit configuration for interleaving and the states of the interference signal and the k-clock according to the present invention. Accordingly, in the present embodiment, if the optical path length difference 82 for the k-clock is set to 11 mm or more in air, which is twice the depth range of the tomographic image, the depth range of the tomographic image can be 5.5 mm or more in air (4.0 mm or more within the eyeball).

Here, a configuration may be employed in which an interleave controller provided in the converter 32 for generating the clock having the n-times frequency switches the interleaving operation, as illustrated in FIG. 10. For example, a plurality of configuration patterns, such as a pattern in which the number of A/D converters that are used is one, a pattern in which the number thereof is two, and a pattern in which the number thereof is four, may be prepared, and control may be performed to switch between the patterns in accordance with the depth range of the tomographic image.

As described above, it is very beneficial for an SS-OCT apparatus to obtain an interference signal at equal wavenumber intervals to attain high image quality. However, even in a case where the k-clock is generated at equal wavenumber intervals using the k-clock interferometer, a frequency higher than the clock frequency is used as the depth range extends, and a problem in which the equal wavenumber property is impaired arises in the process of transmitting the clock. Although the clock frequency can be reduced by half by performing the above-described interleaving operation, in a case where the clock is transmitted as a single-ended signal, when a phase shift is produced due to a distortion in the signal wave form during transmission, the equal wavenumber property is impaired, which causes a noise on the tomographic image (see FIG. 9A).

Therefore, to lessen the impact of a distortion in the waveform during transmission, it is desirable to transmit the k-clock as a differential signal 85 (see FIG. 6), such as a low voltage differential signaling (LVDS) signal. In other words, it is desirable to transmit the single signal through two signal lines (see FIGS. 9B and 9C). When the two signal lines are connected as a pair of signal lines on the positive side and the negative side having a phase difference of 180 degrees, the potential difference between the signal lines corresponds to the signal level, and an external in-phase noise is cancelled (see FIG. 9D). By transmitting the k-clock as the differential signal 85, the through rate is doubled, and the degree of uncertainty of the timing is reduced by half compared to the case of a single-ended signal. Accordingly, transmission can be performed while the equal wavenumber property is maintained with higher accuracy. Note that FIGS. 9A to 9D are diagrams for describing the clock corresponding to the frequency of the k-clock being generated as a differential signal according to the present embodiment.

Here, actual numerical values that can be provided to the present embodiment are used to indicate a necessary sample frequency. If the depth range (measurement distance) of a tomographic image is denoted by $\Delta z$, the center wavelength is denoted by $\lambda c$, and the swept wavelength width is denoted by $\Delta \lambda$, then, the number of samples N, which is the number of times sampling is performed in a single sampling operation over the entire depth range of the tomographic image, is calculated by using an expression, $(4 \times \Delta z \times \Delta \lambda)/\lambda c^2$. If the wavelength sweeping frequency is denoted by fA, and the duty ratio (a period in which effective light emission is performed as OCT during a single sweeping operation) is denoted by d, then, the k-clock frequency fs is calculated by using an expression, $(N \times fA)/d$. In the light source according to the present embodiment, it is assumed that $\lambda c$ is equal to 1040 nm, $\Delta \lambda$ is equal to 110 nm, fA is equal to 100 kHz, and d is equal to 0.446.

Then, in a case where the depth range of a tomographic image is 5.5 mm in air (4.0 mm within the eyeball), the number of samples N is equal to 2237 $((4 \times 5.5 \times 10^6 \times 110)/1040^2=2237)$. In this case, the k-clock frequency fs is equal to 501.57 MHz $((2237 \times 100 \times 10^3)/0.446=501.57)$. Here, sampling is performed by performing interleaving using two A/D converters, and therefore, the clock frequency for one A/D converter is 250.64 MHz (501.57 MHz/2=250.64 MHz).

In a case where the present embodiment is applied to the configuration of the above-described existing OCT apparatus available on the market, the following is attained. In a case where the depth range is 3.6 mm in air (2.6 mm within the eyeball) as in the related art, the number of samples N is equal to 1464 $((4 \times 3.6 \times 10^6 \times 110)/1040^2=1464)$. In this case, the k-clock frequency fs is equal to 328.25 MHz $((1464 \times 100 \times 10^3)/0.446=328.25)$. In the case where sampling is performed by performing interleaving using two A/D converters according to the present embodiment, the number of samples N is equal to 2928 (1464×2=2928), and the k-clock frequency fs is equal to 656.5 MHz (328.25× 2=656.5). Accordingly, a tomographic image having a depth range of 7.2 mm in air (5.2 mm within the eyeball) can be obtained.

As described above, when the configuration of the present embodiment is employed, the depth range of a tomographic image of 5.5 mm in air (4.0 mm within the eyeball), which is used in wide-angle image capturing over an angle of view of 47 degrees or more, can be attained with a clock frequency of 250.64 MHz per A/D converter, which is lower than a frequency of 328.25 MHz of the k-clock used by an existing OCT apparatus available on the market, without deterioration of image quality caused by a phase shift due to a distortion in the signal wave form during transmission of the clock signal. Even when the clock frequency per A/D converter is 328.25 MHz, which is the frequency used by an existing OCT apparatus available on the market, a tomographic image having a depth range of 7.2 mm in air (5.2 mm within the eyeball) can be obtained. That is, it is possible to comprehensively obtain a tomographic image of the fundus in a desired depth range with a single scan operation over a wide area of the fundus.

Note that the present invention is not limited to a single scan operation over a wide area of the fundus. That is, the present invention is not limited to the case where the scanning unit is configured to scan the irradiation light across the fundus over the scan angle that is equal to or larger than 47 degrees in terms of the angle in air. Regardless of the scan angle, in a case where a tomographic image of the fundus in a range equal to or larger than 4.0 mm within the eyeball in the depth range is to be obtained, the k-clock generator is configured so that the optical path length difference corresponds to the range of 4.0 mm or more within the eyeball by taking into consideration sampling that is performed by performing interleaving. Here, as described above, if the second optical path is configured by using a single path, and sampling is performed by performing inter- leaving using two clocks having phases shifted from each other by 180 degrees and two A/D converters, the k-clock generator may be configured so that the optical path length difference is 11 mm or more in air. If the second optical path is configured by using a double path, the k-clock generator may be configured so that the optical path length difference is 5.5 mm or more in air. Even if the k-clock generator is configured so that the number of times sampling is performed or the clock frequency is changed alternatively instead of the optical path length difference being set to any of the lengths described above, a similar effect can be attained.

The optical path length difference 82 for the k-clock may be set to 13.8 mm in air in the case where the second optical path is configured by using a single path or to 6.9 mm in air in the case where the second optical path is configured by using a double path. Then, the depth range of the tomographic image can be 6.9 mm or more in air (5.0 mm or more within the eyeball). The optical path length difference 82 for the k-clock may be set to 16 mm in air in the case where the second optical path is configured by using a single path or to 8 mm in air in the case where the second optical path is configured by using a double path. Then, the depth range of the tomographic image can be 8.0 mm or more in air (5.8 mm or more within the eyeball).

The imaging apparatus according to the present embodiment may further include a selection unit that selects an image capture mode from among a plurality of image capture modes corresponding to different scan angles. Here, the controller may control the scanning unit to change the scan angle in accordance with the selected image capture mode. For example, the scan angle may be set to a first angle, which is equal to or larger than 47 degrees, in an image capture mode (wide-angle-of-view image capture mode) in which an image that includes both the macula and the optic disc is captured as a tomographic image, and may be changed to a second angle, which is smaller than 47 degrees, in an image capture mode (narrow-angle-of-view image capture mode) in which an image that includes one of the macula and the optic disc is captured.

At this time, the selection unit may simultaneously change the depth range from a first range, which is equal to or larger than 4.0 mm within the eyeball, to a second range, which is smaller than 4.0 mm within the eyeball, in accordance with the change in the scan angle. The configuration of the k-clock generator for changing the depth range is described below with reference to FIG. 6.

As described above, the k-clock frequency corresponds to the optical path length difference 82 of the k-clock interferometer. In the second optical path having the optical path length difference relative to the first optical path, the optical path length difference can be changed by using the following methods. For example, a substance (a gas or the like) with which the refractive index can be changed may be provided. In a configuration in which light is emitted from a fiber to air and thereafter enters another fiber, the optical distance between the fibers may be changed. In this configuration in which light is once emitted outside a fiber, a plurality of folding mirrors may be provided on a movable stage and the folding mirrors may be moved in the optical axis direction.

Here, the controller controls the scanning unit and the change unit to change the scan angle and the optical path length difference in accordance with the selected image capture mode. The change unit may be configured to change the optical path length difference from the first optical path length difference, which is 11 mm or more, to a second optical path length difference, which is less than 11 mm, when an interleaving operation is used, for example. This control performed on the change unit is also used in switching of the depth range of the tomographic image associated with switching of the interleaving operation by the interleave controller in the tomographic image obtaining unit described above.

The selection unit may be configured to be able to select an image capture mode from among the plurality of image capture modes including an image capture mode (vitreous body observation mode) in which an image is captured that includes the vitreous body, the retina, and the choroid of the eye. If the image capture mode in which an image is captured that includes the vitreous body, the retina, and the choroid of the eye is selected, a tomographic image of the fundus in a range equal to or larger than 4.0 mm within the eyeball in the depth range may be obtained, for example. Here, it is not essential to make the image capture range have a wider angle; however, making the angle wider is effective in switching of the depth range in this image capture mode. This is because, to capture a tomographic image that includes the vitreous body, the retina, and the choroid of the eye without omission, the range of 4.0 mm or more within the eyeball in the depth range is used.

In a case where the depth range for image capturing is changed in accordance with selection of any mode from among the image capture modes, even if the k-clock generator is configured so that the number of times sampling is performed or the clock frequency is changed alternatively instead of the optical path length difference being changed as described above, a similar effect can be attained. Here, in this alternative process, the k-clock generator may be configured to decrease the number of times sampling is performed or the clock frequency in a case of narrowing the depth range, for example. However, merely by decreasing the number of pieces of data used, such as simply omitting some of the pieces of data, an effect can be attained, that is, the time taken to calculate the distance data upon an A-scan can be reduced.

The present invention is also implemented by performing a process described below. In the process, software (program) for implementing the functions of the embodiment described above is supplied to a system or an apparatus via a network or various storage media, and a computer (or a central processing unit (CPU) or a micro processing unit (MPU)) of the system or the apparatus reads and execute the program.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-175020 filed Sep. 4, 2015, which is hereby incorporated by reference herein in its entirety.

What is claimed is:

1. An imaging apparatus comprising:
a light source configured to emit light while sweeping a wavelength of the light;
an interference unit configured to split the light emitted from the light source into irradiation light with which a fundus is irradiated and reference light and to generate interference light obtained by interference of reflection light reflected from the fundus irradiated with the irradiation light with the reference light;
a scanning unit configured to scan the irradiation light on the fundus;
a detector configured to detect the interference light;
a converter configured to convert an analog signal generated from the interference light into a digital signal;
a clock generator configured as an interferometer including an optical path through which part of the light emitted from the light source passes, the optical path being split into a first optical path and a second optical path having an optical path length difference relative to the first optical path, to generate a clock used by the converter sampling the analog signal at a frequency corresponding to the optical path length difference; and
a tomographic image obtaining unit configured to obtain a tomographic image of the fundus by using the digital signal converted from the analog signal sampled by the converter in accordance with the generated clock, wherein
the scanning unit is configured to scan the irradiation light across the fundus over a scan angle equal to or larger than 47 degrees in air, and
the converter includes n analog/digital converters, n being an integer equal to or larger than 2, and is configured to change at least one of phases of n clocks obtained from the clock having the frequency corresponding to the optical path length difference to produce a phase difference between the phases, and to sample the analog signal in accordance with a clock having a frequency that is n times as high as the frequency corresponding to the optical path length difference by the n analog/digital converters using the n clocks and n analog signals obtained from the analog signal.

2. The imaging apparatus according to claim 1, wherein the clock generator is configured to generate the clock having the frequency corresponding to the optical path length difference as a differential signal, and
the converter is configured to change at least one of phases of the n clocks obtained from the generated differential signal to produce a phase difference between the phases.

3. The imaging apparatus according to claim 1, wherein the converter is configured to switch the clock used to sample the analog signal by switching the number of analog/digital converters that are used in accordance with a depth range of the tomographic image.

4. The imaging apparatus according to claim 1, further comprising:
a controller configured to control the scanning unit to change the scan angle to a first angle, which is 47 degrees or more, or to a second angle, which is less than 47 degrees.

5. The imaging apparatus according to claim 4, further comprising:
a selection unit configured to select an image capture mode from among a plurality of image capture modes including a narrow-angle-of-view image capture mode in which an image of one of a macula and an optic disc of the fundus is captured, wherein
the controller is configured to control the scanning unit to scan the irradiation light over the second angle in a case where the narrow-angle-of-view image capture mode is selected.

6. The imaging apparatus according to claim 5, wherein the plurality of image capture modes further include a wide-angle-of-view image capture mode in which an image of the macula and the optic disc of the fundus is captured, and
the controller is configured to control the scanning unit to scan the irradiation light over the first angle in a case where the wide-angle-of-view image capture mode is selected.

7. The imaging apparatus according to claim 6, wherein the converter is configured to switch the clock having the n-times frequency so that a depth range of the tomographic image falls within a first range, which is 4.0 mm or more, in a case where the wide-angle-of-view image capture mode is selected, and so that the depth range of the tomographic image falls within a second range, which is less than 4.0 mm, in a case where the narrow-angle-of-view image capture mode is selected.

8. The imaging apparatus according to claim 6, wherein the plurality of image capture modes further include a vitreous body observation mode for observing a vitreous body of the fundus,
the controller is configured to control the scanning unit to scan the irradiation light over the second angle in a case where the vitreous body observation mode is selected, and
the converter is configured to switch the clock having the n-times frequency so that a depth range of the tomographic image falls within a range, which is 4.0 mm or more.

9. The imaging apparatus according to claim 1, wherein the converter is configured to switch the clock having the n-times frequency so that a depth range of the tomographic image switches between a first range, which is 4.0 mm or more, and a second range, which is less than 4.0 mm.

10. The imaging apparatus according to claim 1, wherein the tomographic image obtaining unit is configured to obtain the tomographic image having a narrow depth range by omitting one or more pieces of data among pieces of data obtained by the converter performing sampling in accordance with the clock having the n-times frequency and performing Fourier transform on pieces of data remaining after such omission.

11. An imaging apparatus comprising:
a light source configured to emit light while sweeping a wavelength of the light;
an interference unit configured to split the light emitted from the light source into irradiation light with which a fundus is irradiated and reference light and to generate interference light obtained by interference of reflection light reflected from the fundus irradiated with the irradiation light with the reference light;
a detector configured to detect the interference light;
a converter configured to convert an analog signal generated from the interference light into a digital signal;
a clock generator configured as an interferometer including an optical path through which part of the light emitted from the light source passes, the optical path being split into a first optical path and a second optical path having an optical path length difference relative to the first optical path, to generate a clock used by the converter sampling the analog signal at a frequency corresponding to the optical path length difference; and
a tomographic image obtaining unit configured to obtain a tomographic image of the fundus by using the digital signal converted from the analog signal sampled by the converter in accordance with the generated clock, wherein
the converter includes n analog/digital converters, n being an integer equal to or larger than 2, and is configured to change at least one of phases of n clocks obtained from the clock having the frequency corresponding to the optical path length difference to produce a phase difference between the phases, and to sample the analog signal in accordance with a clock having a frequency that is n times as high as the frequency corresponding to the optical path length difference by the n analog/digital converters using the n clocks and n analog signals obtained from the analog signal.

12. The imaging apparatus according to claim 11, wherein the clock generator is configured to generate the clock having the frequency corresponding to the optical path length difference as a differential signal, and
the converter is configured to change at least one of phases of the n clocks obtained from the generated differential signal to produce a phase difference between the phases.

13. The imaging apparatus according to claim 1, wherein the converter is configured to make the phase difference equal to 180 degrees.

14. The imaging apparatus according to claim 11, wherein the converter is configured to make the phase difference equal to 180 degrees.

15. An imaging apparatus comprising:
a light source configured to emit light while sweeping a wavelength of the light;
an interference unit configured to split the light emitted from the light source into irradiation light with which a fundus is irradiated and reference light and to generate interference light obtained by interference of reflection light reflected from the fundus irradiated with the irradiation light with the reference light;
a detector configured to detect the interference light;
a converter configured to convert an analog signal generated from the interference light into a digital signal;
a clock generator configured as an interferometer including an optical path through which part of the light emitted from the light source passes, the optical path being split into a first optical path and a second optical path having an optical path length difference relative to the first optical path, to generate a clock used by the converter sampling the analog signal at a frequency corresponding to the optical path length difference; and a tomographic image obtaining unit configured to obtain a tomographic image of the fundus by using the digital signal converted from the analog signal sampled by the converter in accordance with the generated clock, wherein the converter includes an inverter circuit configured to invert, in relation to one of two clocks obtained from the clock having the frequency corresponding to the optical path length difference, the other of the two clocks, a first analog-to-digital (A/D) converter configured to sample the analog signal using the one, and a second analog-to-digital (A/D) converter configured to sample the analog signal using the inverted other.

16. The imaging apparatus according to claim 1, wherein the clock generator is configured to generate a differential signal by inverting, in relation to one of two clocks obtained from the clock having the frequency corresponding to the optical path length difference, the other of the two clocks.

17. The imaging apparatus according to claim 11, wherein the clock generator is configured to generate a differential signal by inverting, in relation to one of two clocks obtained from the clock having the frequency corresponding to the optical path length difference, the other of the two clocks.

18. The imaging apparatus according to claim 13, wherein n is equal to 2,
wherein the converter includes an inverter circuit configured to invert the other of the two clocks in relation to the one of the two clocks, and
wherein the phase difference of 180 degrees is produced by the inverter circuit.

19. The imaging apparatus according to claim 14, wherein n is equal to 2,
the converter includes an inverter circuit configured to invert the other of the two clocks in relation to the one of the two clocks, and
the phase difference of 180 degrees is produced by the inverter circuit.

20. The imaging apparatus according to claim 15, further comprising:
signal lines configured to transmit two clocks to the converter, the two clocks being obtained from the clock having the frequency corresponding to the optical path length difference, wherein
the clock generator is configured to generate a differential signal by inverting, in relation to one of the two clocks, the other of the two clocks and by connecting the signal lines as one signal line such that a noise generated in the two transmitted clocks is cancelled.

21. The imaging apparatus according to claim 15, wherein the converter samples the analog signal in accordance with a clock having a frequency that is twice as high as the frequency corresponding to the optical path length difference by sampling the analog signal by the first A/D converter and the second A/D converter.

22. The imaging apparatus according to claim 15, wherein the converter samples the analog signal using both a rising edge and a falling edge of the clock by sampling the analog signal by the first A/D converter and the second A/D converter.

23. The imaging apparatus according to claim 15, wherein the clock generator is configured to generate a differential signal by inverting, in relation to one of two clocks obtained from the clock having the frequency corresponding to the optical path length difference, the other of the two clocks.

24. The imaging apparatus according to claim 15, wherein the depth range of the tomographic image is 4.0 mm or more within the eyeball.

25. The imaging apparatus according to claim 15, wherein the depth range of the tomographic image is 5.0 mm or more within the eyeball.

26. The imaging apparatus according to claim 15, wherein the depth range of the tomographic image is 5.8 mm or more within the eyeball.

27. The imaging apparatus according to claim 15, further comprising;
a scanning unit configured to scan the irradiation light on the fundus;
wherein the scanning unit is configured to scan the irradiation light across the fundus over a scan angle equal to or larger than 47 degrees in air.

28. The imaging apparatus according to claim 15, further comprising;
a scanning unit configured to scan the irradiation light on the fundus;
wherein the scanning unit is configured to scan the irradiation light across the fundus over a scan angle equal to or larger than 47 degrees in air.

29. The imaging apparatus according to claim 15, wherein the converter samples the analog signal at equal wave-number intervals.

30. The imaging apparatus according to claim 20, wherein the converter samples the analog signal at equal wave-number intervals.

31. The imaging apparatus according to claim 11, wherein the converter samples the analog signal at equal wave-number intervals.

32. The imaging apparatus according to claim 1, wherein the converter samples the analog signal at equal wave-number intervals.

* * * * *